United States Patent [19]

Becher et al.

[11] Patent Number: 4,622,340

[45] Date of Patent: Nov. 11, 1986

[54] UREA DERIVATIVES AND PESTICIDAL COMPOSITIONS CONTAINING SAME

[75] Inventors: Heinz-Manfred Becher, Bingen; Ricarda Prokic-Immel, Mainz; Walter Wirtz, Darmstadt, all of Fed. Rep. of Germany

[73] Assignee: Celamerck GmbH & Co., KG, Ingelheim am Rhein, Fed. Rep. of Germany

[21] Appl. No.: 604,371

[22] Filed: Apr. 26, 1984

Related U.S. Application Data

[63] Continuation-in-part of Ser. No. 321,446, Nov. 16, 1981, Pat. No. 4,457,943.

[30] Foreign Application Priority Data

Nov. 22, 1980 [DE] Fed. Rep. of Germany ....... 3044055
Jun. 15, 1981 [DE] Fed. Rep. of Germany ....... 3123720

[51] Int. Cl.$^4$ .................... A01N 47/28; C07C 127/22; C07C 157/12
[52] U.S. Cl. ..................... 514/594; 564/23; 564/44
[58] Field of Search ............ 564/23, 44; 424/322; 514/594, 550

[56] References Cited

U.S. PATENT DOCUMENTS 4,276,310 6/1981 Sirrenberg et al. ............ 564/23 X
4,310,548 1/1982 Ehrenfreund ................. 424/322
4,399,152 8/1983 Brouwer et al. .............. 564/44 X

*Primary Examiner*—Robert V. Hines
*Attorney, Agent, or Firm*—Hammond & Littell, Weissenberger & Dippert

[57] ABSTRACT

This invention relates to compounds of the formula

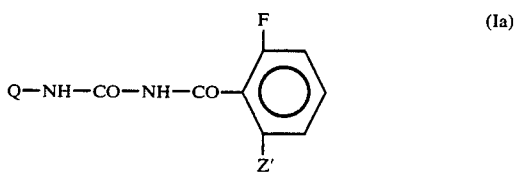

wherein

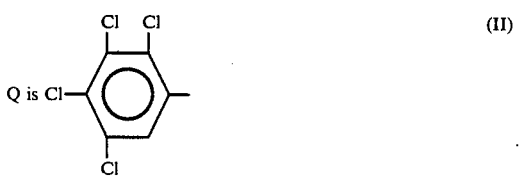

or

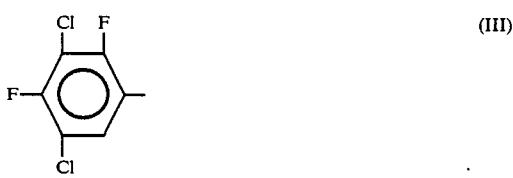

and

Z' is chlorine or fluorine, with the proviso that Z' is chlorine when Q is the moiety of Formula III. The invention also relates to the preparation of the compounds, their use in controlling animal pests in plant protection, and pesticidal agents comprising the compounds as active ingredients.

6 Claims, No Drawings

UREA DERIVATIVES AND PESTICIDAL COMPOSITIONS CONTAINING SAME

CROSS-REFERENCE TO RELATED APPLICATION

This application is a continuation-in-part of co-pending U.S. patent application Ser. No. 321,446, filed Nov. 16, 1981 and now U.S. Pat. No. 4,457,943.

FIELD OF THE INVENTION

This invention is directed to urea derivatives. More particularly, this invention is directed to N-(tetrasubstituted phenyl)-N'-(disubstituted benzoyl)-urea derivatives, pesticidal compositions containing them, and their use as pesticides.

DETAILED DESCRIPTION OF THE INVENTION

This invention is directed to novel urea derivatives of the general formula

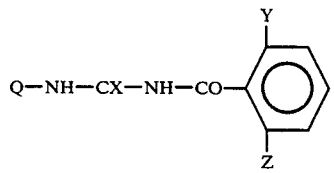
(I)

wherein

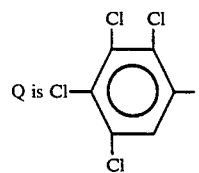
(II)

Q is or

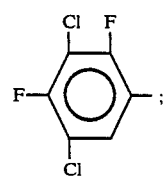
(III)

X is oxygen or sulfur;
Y is chlorine or fluorine; and
Z is hydrogen, chlorine, or fluorine.

The invention is also directed to the preparation of the compounds of Formula I, their use in controlling animal pests in plant protection, and pesticidal agents comprising the compounds of Formula I as active ingredients.

German Auslegeschrift No. 2,123,236 discloses benzylureas which are effective against animal pests. The compound of the formula

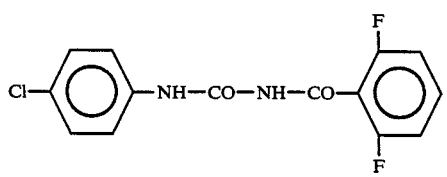

described in said German Auslegeschrift is a commercial product (diflubenzurone). In comparison to this compound, the compounds according to the invention exhibit a distinctly superior effect, for example, against insects in the larval stage.

The compounds of Formula I can be prepared according to methods known per se:

Method A

An aniline of the formula $$Q-NH_2 \quad (IV)$$

wherein Q is as described above is reacted with an isocyanate or isothiocyanate of the formula

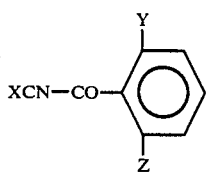
(V)

wherein X, Y, and Z are as described above.

Method B

An isocyanate or isothiocyanate of the formula $$Q-NCX \quad (VI)$$

wherein Q and X are as described above, is reacted with a benzamide of the formula

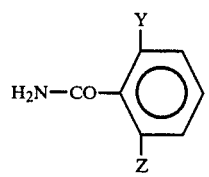
(VII)

wherein Y and Z are as described above.

The reactions according to Method A or B are carried out at temperatures between ambient temperature and the boiling point of the reaction mixture. The reaction medium used is an inert solvent, for example, an aromatic hydrocarbon, such as toluene or xylene, or chlorobenzene, pyridine, or an ether such as dioxane or tetrahydrofuran, optionally in the presence of a tertiary organic base (triethylamine or pyridine).

The starting materials, if they have not been previously described, can be obtained by conventional methods. The aniline of Formula IV is obtained from the corresponding nitro compound by reduction of the nitro group with the reducing agents customary for this purpose. Reaction of the aniline of Formula IV with phosgene or thiophosgene results in the isocyanate or isothiocyanate of Formula VI.

Benzoyl isocyanates of Formula V can be obtained from the corresponding benzamides and oxalyl chloride, and benzoyl isothiocyanates of Formula V from the corresponding benzoyl chlorides and potassium thiocyanate.

A preferred embodiment of the invention directed to compounds that are particularly effective comprises the compounds of the formula

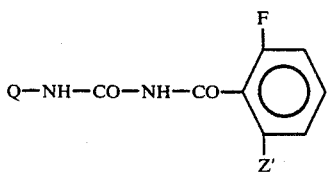

(Ia)

wherein Q is as described above and Z' is chlorine or fluorine, with the proviso that Z' is chlorine when Q is the moiety of Formula III. More specifically, preferred compounds include N-(2,-3,4,5-tetrachlorophenyl)-N'-(2,6-difluorobenzoyl)-urea, N-(2,4-difluoro-3,5-dichlorophenyl)-N'-(2-chloro-6-fluorobenzoyl)-urea, and N-(2,3,4,5-tetrachlorophenyl)-N'-(2-chloro-6-fluorobenzoyl)-urea.

The novel compounds can be employed for control of insects and acarids. Accordingly, they are useful as active ingredients of insecticides and acaricides which can be employed against harmful insects and mites as well as against the developmental stages of such insects and mites, such as caterpillars and larvae. Not only harmful acarids but also, in particular, harmful insects from the groups of Diptera, Coleoptera, Lepidoptera, Hemiptera, Homoptera, and Hymenoptera can be controlled. Specific examples include the following: mosquitoes (Aedes), the Mexican bean beetle (Epilachna), the Colordao beetle (Leptinotarsa), the diamondback moth (Plutella), the armyworm (Prodenia), the spider mites (Tetranychus), the bulb scale mites (Tarsonemus), the palmerworm (Dichomeris), small butterflies (Pyroderces), Argyroplose ocellana, winter-moth, tortrix moths, Summer fruit tortrix moth (Adoxophyes reticulana), clothes moths, green oak tortrix moths, vine leaf roller, pinworm, corn borer, boll-weevil, pear sawfly, and beet-lear miner.

When the compounds according to the invention are to be used as pesticidal agents, that is, as active ingredients in pesticidal compositions, the compounds are processed with customary excipients and/or carriers to form conventional formulations, such as, for example, emulsion concentrates, wettable powders, or dusts. The compounds are used in the form of sprays and dusts with active ingredient, that is, active substance, concentrations of from about 0.005 to 2% by weight, or in the form of ultra-low volume formulations also with high concentrations of active substance (up to about 90% by weight). The dosage per hectare, which is dependent upon the active ingredient employed and upon the crop treated, amounts to from about 0.005 to 0.5 kg, preferably from about 0.01 to 0.25 kg, of active substance per carrier.

FORMULATION EXAMPLE

| Wettable Powder | |
| --- | --- |
| Component | % by Weight |
| Active ingredient according to invention | 25 |
| Kaolin | 55 |
| Colloidal silica | 10 |
| Lignin sulfonate (dispersing agent) | 9 |
| Sodium tetrapropylene benzene-sulfonate (wetting agent) | 1 |

The components are processed to a wettable suspension powder (particle size <4μ) in conventional manner. For application, a spray mixture containing from about 0.0005 to 0.05% by weight of active ingredient, based on the weight of the total spray mixture, in water is prepared.

It is contemplated that any compound of Formula I, or even a combination thereof, could be used as active ingredient in compositions useful according to the invention, such as the wettable powder set forth above. It is also contemplated that the amount of active ingredient in such compositions may be varied to achieve the effective range set forth above. Moreover, the amount and nature of the inert carrier ingredients may be varied to meet particular requirements.

The superior effectiveness of compounds according to the invention has been demonstrated by comparison testing with known compounds such as, for example, the commercial product difluobenzurone, mentioned above. The testing was as follows:

COMPOUNDS TESTED

According to the invention

I: N-(2,4-difluoro-3,5-dichlorophenyl)-N'-(2-chloro-6-fluorobenzoyl)-urea

II: N-(2,4-difluoro-3,5-dichlorophenyl)-N'-(2-chlorobenzoyl)-thiourea

III: N-(2,3,4,5-tetrachlorophenyl)-N'-(2,6-difluorobenzoyl)-urea

IV: N-(2,3,4,5-tetrachlorophenyl)-N'-(2-chlorobenzoyl)-thiourea

V: N-(2,3,4,5-tetrachlorophenyl)-N'-(2-chloro-6-fluorobenzoyl)-urea

VI: N-(2,4-difluoro-3,5-dichlorophenyl)-N'-(2,6-difluorobenzoyl)-urea

Comparison

A: N-(2,-3,4,5-tetrafluorophenyl)-N'-(2,6-difluorobenzoyl)-urea [prepared according to U.S. Pat. No. 4,310,548]

B: N-(2,3,4,6-tetrafluorophenyl)-N'-(-b 2,6-difluorobenzoyl)-urea [prepared according to U.S. Pat. No. 4,310,548]

C: N-(4-chlorophenyl)-N'-(2,6-difluorobenzoyl)-urea [known as difluobenzurone; described in DE-AS No. 2,123,236]

D: N-(2,4,5-trichlorophenyl)-N'-(2,6-dichlorobenzoyl)-urea [according to U.S. Pat. No. 3,748,356]

E: N-(2,4,5-trichlorophenyl)-N'-(2,6-difluorobenzoyl)-urea [according to U.S. Patent No. 3,748,356]

PROCEDURE

The effects of Compounds I to VI and A to E as active ingredients were tested with regard to gnat larvae (Aedes aegyptii L; larvae four days old) and Egypt cotton caterpillars (Spodoptera littoralis Boids.; caterpillars weighing about 10 mg apiece). The specific testing proceeded as follows:

A Aegyptii

The active ingredients were dissolved in acetone, and dilutions were prepared, the individual concentrations of which were diluted with water to 200 ml each. The resulting solutions were then poured into glass dishes about 20 cm in diameter and having a depth of about 6 cm. After 25 mosquito larvae were added to each dish, the dishes were covered. Each experiment was carried out in duplicate. The larvae and papae mortality was determined within 7 to 10 days.

S. littoralis

Shoots of horsebeans (Vicia faba var.) were dipped in different concentrations of aqueous emulsions of the test compounds. The shoots were dried and stocked with ten caterpillars each. After three days, fresh, untreated leaf shoots were supplied as feed, and after six days, the mortality was determined.

RESULTS AND EVALUATION

In initial testing, the LD$_{95}$, in ppm of active ingredient, for each of Compounds I to V and C was determined in greenhouse testing where the sprays were prepared from about 0.1 to 0.5% solutions of the active ingredients in acetone by dilution with appropriate quantities of water. The test results are set forth in the following table:

TABLE 1

| Active Ingredient | A. aegyptii LD$_{95}$ (ppm) | S. littoralis LD$_{95}$ (ppm) |
| --- | --- | --- |
| Compound C* | 0.0031 | 3.4 |
| Compound I | 0.0016 | 0.042 |
| Compound II | — | 0.30 |
| Compound III | 0.00084 | 0.3 |
| Compound IV | — | 0.4 |
| Compound V | 0.00094 | 0.65 |

*Comparison

After further testing, mortality figures, determined in percents, were converted into probit figures, and from these values and from the concentrations the LC$_{95}$ values were determined graphically. In the table below, the columns designated as "Ratio" indicate the relative effectiveness of the various compounds, where the effectiveness of the strongest comparative compound was taken to be 1.00. The results of this testing were as follows:

TABLE 2

| Active Ingredient | A. aegyptii | | S. littoralis | |
| --- | --- | --- | --- | --- |
| | LC$_{95}$ (ppm) | Ratio | LC$_{95}$ (ppm) | Ratio |
| Compound A* | 0.023 | 0.196 | 0.025 | 1.00 |
| Compound B* | 0.39 | 0.012 | 0.42 | 0.060 |
| Compound C* | 0.0045 | 1.00 | 2.5 | 0.010 |
| Compound D* | 0.2 | 0.023 | 20.0 | 0.0013 |
| Compound E* | 0.0054 | 0.083 | 0.042 | 0.60 |
| Compound I | 0.0016 | 2.81 | — | — |
| Compound III | 0.00085 | 5.29 | — | — |
| Compound V | 0.00094 | 4.79 | — | — |
| Compound VI | 0.00085 | 5.29 | 0.013 | 1.92 |

*Comparison

Even in the most unfavorable case (comparison of Compound VI versus Compound A against S. littoralis), about twice the active ingredient concentration of the comparison compound has to be used to achieve a 95% mortality rate. Moreover, Compounds I, III, V, and VI are especially effective as compared to Compounds A to E against A. aegyptii.

The following examples are intended to illustrate the invention and are not to be construed as limiting the invention thereto.

EXAMPLES

PREPARATION OF STARTING MATERIALS

EXAMPLE 1

2,4-Difluoro-3,5-dichloro-nitrobenzene

Two hundred fifty grams of anhydrous potassium fluoride (dried by calcination for several hours at 600° C.) at about 200° C. were introduced into a solution of 261 gm (1.0 mol) of 2,3,4,5-tetrachloronitrobenzene in 1000 ml of pure anhydrous dimethylformamide (dried with P$_2$O$_5$ and subsequently with a molecular sieve). The resulting mixture was stirred thoroughly for 15 hours at 140° C. It was then allowed to cool to 40° C., and the undissolved matter was removed by suction filtration and rinsed with dimethylformamide. The solvent was distilled from the combined filtrates under reduced pressure, through a column. The distillation residue was dissolved in 1.5 liters of diisopropyl ether. The solution thus obtained was extracted by shaking with saturated aqueous sodium bicarbonate solution, using a 250 ml amount each of three times. It was then dried with magnesium sulfate and concentrated by evaporation to leave a residue which was distilled under a water pump vacuum.

Yield: 142 gm (0.62 mol; 62% of theory),
B.p.: 119°–122° C./20 mbar.

EXAMPLE 2

2,4-Difluoro-3,5-dichloroaniline

One hundred forty grams (2.5 mols) of iron powder was introduced, with stirring, into a mixture of 114 gm (0.50 mol) of 2,4-difluoro-3,5-dichloro-nitrobenzene, 2 liters of water, and 10 ml of acetic acid at 95° to 100° C. The reaction mixture thus obtained was thoroughly stirred for eight hours at 95° to 100° C. Fifty milliliters of 40% sodium hydroxide solution were then added, and the mixture was steam-distilled. The difluorodichloroaniline produced passed over, that is, was distilled off, together with water. After completion of the distillation, the product was isolated from the heterogeneous distillate by extraction with ethylene chloride. The solvent was distilled from the organic phase and the product which remained was distilled in a water pump vacuum.

Yield: 91.5 gm (0.46 mol; 92% of theory),
B.p.: 118°–121° C./20 mbar.

EXAMPLE 3

2,4-Difluoro-3,5-dichlorophenyl isocyanate

Hydrogen chloride was passed into a well-stirred solution of 39.6 gm (0.20 mol) of 2,4-difluoro-3,5-dichloroaniline in 400 ml of toluene until a precipitate no longer separated out. The heterogeneous mixture thus obtained was cooled to 5° to 10° C. At this temperature, 40 gm (0.4 mol) of phosgene were passed in, with stirring. The mixture was then heated slowly, with stirring, so that after about two hours a temperature of 100° to 105° C. was reached. Stirring was then continued for seven hours at this temperature. During this time, a clear solution was formed, and hydrogen chloride was liberated. Nitrogen was then passed into the mixture for one hour at the same temperature to drive off the excess phosgene. Thereafter the solvent was distilled off, in vacuo at the end. The crude product which remained was distilled in a water pump vacuum.

Yield: 35.4 gm (0.158 mol; 79% of theory),
B.p.: 100°–104° C./20 mbar.

EXAMPLE 4

2,6-Difluorobenzoyl isocyanate

Twenty-eight grams (0.22 mol) of oxalyl chloride were added dropwise to a solution of 31.4 gm (0.20 mol) of 2,6-difluorobenzamide in 250 ml of toluene. The solution thus obtained was boiled under reflux for five hours, during which time hydrogen chloride and carbon monoxide were liberated. The solvent was then distilled off, in vacuo at the end. The product which remained was distilled in an oil pump vacuum.

Yield: 28.5 gm (0.156 mol; 77% of theory),

B.p.: 54°–56° C./0.7 mbar.

By use of procedures analogous to that described above, the following compounds were obtained:

EXAMPLE 5

2,6-Dichlorobenzoyl isocyanate (boiling point: 75°–78° C./ 0.13 mbar).

EXAMPLE 6

2-Chloro-6-fluorobenzoyl isocyanate (boiling point: 75°–78° C./0.13 mbar).

EXAMPLE 7

2-Chlorobenzoyl isocyanate (boiling point: 73°–77° C./ 0.13 mbar).

EXAMPLE 8

2-Chlorobenzoyl isothiocyanate

Thirty-five grams (0.36 mol) of finely powdered, anhydrous potassium thiocyanate (obtained by drying for several hours at 110° C. and then grinding) were introduced into a solution of 52.5 gm (0.30 mol) of o-chlorobenzoyl chloride in 100 ml of anhydrous toluene. The mixture thus obtained was boiled under reflux for six hours. It was then allowed to cool, insoluble matter was removed by suction filtration, and the filtrate was concentrated to obtain a residue, which is distilled in a water pump vacuum.

Yield: 52 gm (0.26 mol; 87% of theory),
B.p.: 149°–152° C./21 mbar.

PREPARATION OF COMPOUNDS OF FORMULA I

EXAMPLE 9

N-(2,4-Difluoro-3,5-dichlorophenyl)-N'-(2-chlorobenzoyl)-urea

A mixture of 9.0 gm (0.040 mol) of 2,4-difluoro-3,5-dichlorophenyl isocyanate, 6.5 gm (0.042 mol) of 2-chlorobenzamide, and 100 ml of xylene was boiled for five hours under reflux. It was then allowed to cool, and the product which precipitated was removed by suction filtration and dried.

Yield: 14.3 gm (0.0377 mol; 94% of theory),
M.p.: 225°–229° C.

EXAMPLE 10

N-(2,4-Difluoro-3,5-dichlorophenyl)-N'-(2,6-difluorobenzoyl)-urea

Three grams (0.016 mol) of 2,6-difluoro-benzoyl isocyanate were added to a solution of 2.95 gm (0.015 mol) of 2,4-difluoro-3,5-dichloroaniline in 50 ml of toluene. The solution thus obtained was stirred for 15 hours at room temperature. Thereafter, the product which precipitated during that time was removed by suction filtration and dried.

Yield: 4.2 gm (0.011 mol; 73% of theory),
M.p.: 221°–224° C.

By use of procedures analogous to that above, the following compounds were prepared:

EXAMPLE 11

N-(2,4-Difluoro-3,5-dichlorophenyl)-N'-(2,6-dichlorobenzoyl)-urea (melting point: 238°–242° C.).

EXAMPLE 12

N-(2,4-Difluoro-3,5-dichlorophenyl)-N'-(2-chloro-6-fluorobenzoyl)-urea (melting point: 214°–218° C.).

EXAMPLE 13

N-(2,4-Difluoro-3,5-dichlorophenyl)-N'-(2-chlorobenzoyl)-urea (melting point: 228°–232° C.).

EXAMPLE 14

N-(2,4-Di-fluoro-3,5-dichlorophenyl)-N40 -(2-chlorobenzoyl)-thiourea (melting point: 150°–152° C.).

EXAMPLE 15

N-(2,3,4,5-Tetrachlorophenyl)-N'-(2,6-difluorobenzoyl)-urea

An amount of 3.9 gm (0.020 mol) of 2,6-difluorobenzoyl isocyanate was added to a solution of 4 gm (0.017 mol) of vic-tetrachloroaniline in 60 ml of toluene. The resulting solution was stirred for one hour at room temperature. Thereafter, the product which precipitated during that time was removed by suction filtration, washed with toluene, and dried.

Yield: 7 gm (0.017 mol), virtually quantitative,
M.p.: 255°–257° C.

A small proportion of the product was recrystallized from a large amount of acetone.

M.p.: 257°–259° C.

Using procedures analogous to that of Example 15, the following compounds were prepared:

EXAMPLE 16

N-(2,3,4,5-Tetrachlorophenyl)-N'-(2-chloro-6-fluorobenzoyl)-urea (melting point: >250° C.).

EXAMPLE 17

N-(2,3,4,5-Tetrachlorophenyl)-N'-(2-chlorobenzoyl)-thiourea (melting point: 186°–187° C.).

EXAMPLE 18

N-(2,3,4,5-Tetrachlorophenyl)-N'-(2-chlorobenzoyl)-urea (melting point: 247°–248° C.).

EXAMPLE 19

N-(2,3,4,5-Tetrachlorophenyl)-N'-(2,6-difluorobenzoyl)-thiourea.

EXAMPLE 20

N-(2,3,4,5-Tetrachlorophenyl)-N'-(2-chloro-6-fluorobenzoyl)-thiourea.

EXAMPLE 21

N-(2,3,4,5-Tetrachlorophenyl)-N'-(2-fluorobenzoyl)-urea.

EXAMPLE 22

N-(2,3,4,5-Tetrachlorophenyl)-N'-(2-fluorobenzoyl)-thiourea.

EXAMPLE 23

N-(2,3,4,5-Tetrachlorophenyl)-N'-(2,6-dichlorobenzoyl)-urea (melting point: >260° C.).

EXAMPLE 24

N-(2,3,4,5-Tetrachlorophenyl)-N'-(2,6-dichlorobenzoyl)-thiourea.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A compound of the formula

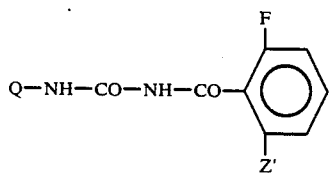

wherein

Q is

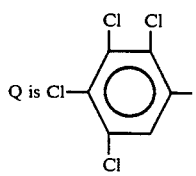

or

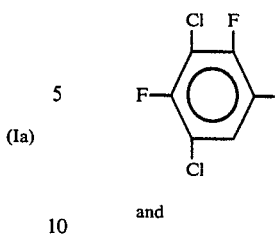

and

Z′ is chlorine or fluorine, with the proviso that Z′ is chlorine when Q is the moiety of Formula III.

2. The compound of claim 1 which is N-(2,3,4,5-tetrachlorophenyl)-N′-(2,6-difluorobenzoyl)-urea.

3. The compound of claim 1 which is N-(2,4-difluoro-3,5-dichlorophenyl)-N′-(2-chloro-6-fluorobenzoyl)-urea.

4. The compound of claim 1 which is N-(2,3,4,5-tetrachlorophenyl)-N′-(2-chloro-6-fluorobenzoyl)-urea.

5. A pesticidal composition consisting essentially of an inert carrier and an effective insecticidal, acaridical, or fungicidal amount of a compound of claim 1.

6. The method of killing insects, acarids, or fungi which comprises contacting same with an effective insecticidal, acaricidal, or fungicidal amount of a compound of claim 1.

* * * * *

UNITED STATES PATENT AND TRADEMARK OFFICE
CERTIFICATE OF CORRECTION

PATENT NO. : 4,622,340

DATED : November 11, 1986

INVENTOR(S) : HEINZ-MANFRED BECHER, RICARDA PROKIC-IMMEL and WALTER WIRTZ

It is certified that error appears in the above-identified patent and that said Letters Patent is hereby corrected as shown below:

Column 3, line 13 - "(2,-3" should read -- (2,3 --.

line 45 - "0.005" should read -- 0.0005 --.

Column 4, line 35 - "(2,-3" should read -- (2,3 --.

line 38 - "(-b 2,6" should read -- (2,6 --.

line 56 - "A Aegyptii" should read -- A. Aegyptii --.

Column 8, line 7 - "-N40-(2-" should read -- -N'-(2- --.

Signed and Sealed this

Seventeenth Day of February, 1987

*Attest:*

DONALD J. QUIGG

*Attesting Officer*      *Commissioner of Patents and Trademarks*